United States Patent
Tsuchikawa et al.

(10) Patent No.: US 8,458,889 B2
(45) Date of Patent: Jun. 11, 2013

(54) ACTUATOR MANUFACTURING METHOD

(75) Inventors: Yutaka Tsuchikawa, Kiyosu (JP);
Takashi Maeno, Kiyosu (JP); Naoto Kuriyama, Kiyosu (JP); Takanori Nakai, Kiyosu (JP); Hiromitsu Takeuchi, Kiyosu (JP); Yoji Kimura, Kiyosu (JP)

(73) Assignee: Toyoda Gosei Co., Ltd., Aichi-pref. (JP)

( * ) Notice: Subject to any disclaimer, the term of this patent is extended or adjusted under 35 U.S.C. 154(b) by 5 days.

(21) Appl. No.: 13/220,930

(22) Filed: Aug. 30, 2011

(65) Prior Publication Data

US 2012/0060355 A1    Mar. 15, 2012

(30) Foreign Application Priority Data

Sep. 15, 2010  (JP) ................................. 2010-206824

(51) Int. Cl.
*G01R 3/00*       (2006.01)
(52) U.S. Cl.
USPC ................ 29/595; 29/602.1; 29/841; 29/855; 29/858; 29/883; 310/311; 310/328; 310/366; 310/369
(58) Field of Classification Search
USPC ............. 29/592.1, 595, 602.1, 841, 855, 858, 29/883; 310/311, 328, 366, 369
See application file for complete search history.

(56) References Cited

U.S. PATENT DOCUMENTS

| 5,494,090 | A | * | 2/1996 | Kejha | 152/310 |
| 6,891,317 | B2 | * | 5/2005 | Pei et al. | 310/328 |
| 7,064,472 | B2 | * | 6/2006 | Pelrine et al. | 310/324 |
| 7,400,080 | B2 | * | 7/2008 | Benslimand et al. | 310/369 |
| 7,895,728 | B2 | * | 3/2011 | Benslimane et al. | 29/595 |
| 8,250,732 | B2 | * | 8/2012 | Benslimane et al. | 29/595 |
| 2003/0006669 | A1 | * | 1/2003 | Pei et al. | 310/309 |
| 2006/0066183 | A1 | * | 3/2006 | Benslimand et al. | 310/369 |
| 2009/0184606 | A1 | * | 7/2009 | Rosenthal et al. | 310/367 |

FOREIGN PATENT DOCUMENTS

| JP | 2007-252132 A | 9/2007 |
| JP | 2009-124875 A | 6/2009 |

* cited by examiner

*Primary Examiner* — Paul D Kim
(74) *Attorney, Agent, or Firm* — Posz Law Group, PLC

(57) ABSTRACT

An actuator manufacturing method includes alternately stacking a plurality of dielectric elastomer layers and a plurality of conductive rubber layers along the direction of thickness to form a sheet, and wrapping the sheet formed about a core to form a rolled sheet. When the sheet formed in the step of alternately stacking is wrapped about the core, the sheet is formed by the dielectric elastomer layers and the conductive rubber layers. Therefore, even if the dielectric elastomer layers in the sheet are made to be thin, the thickness of the entire sheet is prevented from being excessively thin.

9 Claims, 4 Drawing Sheets

ACTUATOR MANUFACTURING METHOD

BACKGROUND OF THE INVENTION

The present invention relates to a method for manufacturing an actuator.

Conventionally, actuators have been known in which the actuator has a sheet formed by stacking dielectric rubber layers (dielectric elastomer layers) and conductive rubber layers along the direction of thickness. This type of actuator is operated by executing and stopping voltage application to the conductive rubber layers of the sheet so that the dielectric elastomer layers are expanded or contracted (refer to Japanese Laid-Open Patent Publication No. 2007-252132).

Such actuators are used for artificial muscles. More specific examples include an actuator disclosed in Japanese Laid-Open Patent Publication No. 2009-124875. The sheet of this actuator is rolled. Voltage application to the conductive rubber layers of the sheet is executed or stopped, so that the rolled sheet is expanded or contracted along the axial direction.

To manufacture the actuator, dielectric elastomer layers and conductive rubber layers may be stacked along the direction of thickness to form a sheet, and the formed sheet may be rolled by being wrapped about a core.

SUMMARY OF THE INVENTION

The above described actuator has a tendency in that the thinner the dielectric elastomer layers of the sheet, the smaller becomes a voltage that needs to be applied to achieve adequate operation of the actuator. To minimize the applied voltage, the thickness of the dielectric elastomer layers in the actuator is desired to be as small as possible.

However, if the dielectric elastomer layers are made thinner to meet such a demand, the sheet, which is formed by the dielectric elastomer layers and conductive rubber layers, becomes also thin. When wrapping the sheet around a core to form a rolled sheet, the wrapping can be uneven along the longitudinal direction of the core. In such a case, the load accompanying the wrapping unevenly acts on the sheet, and can act on thin parts of the dielectric elastomer layers. If the load concentrates on thin parts of the dielectric elastomer layers in the sheet, the dielectric elastomer layers are likely to be torn.

Accordingly, it is an objective of the present invention to provide a method for manufacturing an actuator in which, even if dielectric elastomer layers of a sheet are made thin, the dielectric elastomer layers are not torn when the sheet is wrapped about a core.

To achieve the foregoing objective, the present invention provides a method for manufacturing an actuator formed by rolling a sheet in which dielectric elastomer layers and conductive rubber layers are stacked along a direction of thickness. Voltage application to the conductive rubber layers of the sheet is executed or stopped, so that the rolled sheet is expanded or contracted along the axial direction. The method includes a first step, in which a plurality of dielectric elastomer layers and a plurality of conductive rubber layers are alternately stacked along the direction of thickness to form a sheet, and a second step, in which the sheet formed in the first step is wrapped about a core to form a rolled sheet.

According to the above method, in the second step, when wrapping the single sheet formed in the first step about the core to form a roll, the single sheet is formed by multiple dielectric elastomer layers and multiple conductive rubber layers. Therefore, even if each of the dielectric elastomer layers of the sheet is made thin so as to reduce the voltage applied to the dielectric rubber layers to allow the actuator to operate adequately, the thickness of the single sheet as a whole is prevented from being excessively reduced. When wrapping the single sheet around the core in the second step, the wrapping can be uneven along the longitudinal direction of the core. In such a case, the load accompanying the uneven wrapping acts on the sheet. However, the load is dispersed to the multiple dielectric elastomer layers in the sheet. This prevents the load from concentrating on one of the multiple dielectric elastomer layers in the sheet. Accordingly, the dielectric elastomer layers are prevented from being torn by concentration of the load.

Other aspects and advantages of the present invention will become apparent from the following description, taken in conjunction with the accompanying drawings, illustrating by way of example the principles of the invention.

BRIEF DESCRIPTION OF THE DRAWINGS

The invention, together with objects and advantages thereof, may best be understood by reference to the following description of the presently preferred embodiments together with the accompanying drawings in which.

DETAILED DESCRIPTION OF THE PREFERRED EMBODIMENTS

One embodiment of the present invention will now be described with reference to the drawings.

Figure 1A:
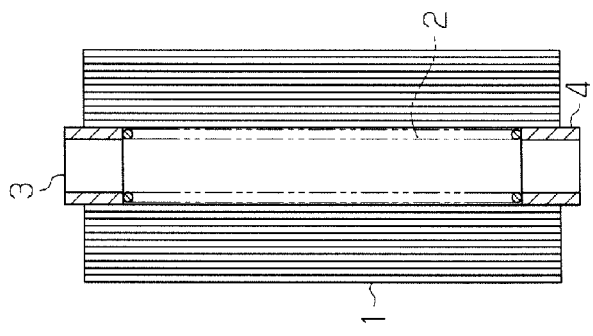
FIGS. 1A to 1C conceptually show the normal state of an actuator, an expanded state of the actuator, and the structure of a sheet of the actuator.

An actuator shown in FIG. 1A is formed by rolling a sheet 1 so that it becomes cylindrical. The cylindrical sheet 1 is expanded and contracted along the axial direction thereof, so that the length along the axial direction is changed. FIG. 1A shows a normal state of the actuator, or a contracted state, and FIG. 1B shows an expanded state of the actuator from the normal state.

As shown in FIG. 1A, a coil spring 2 is arranged in the cylindrical sheet 1. Also, pipes 3, 4 are fixed to the inner circumferential surface of both ends in the axial direction of the sheet 1. The elastic force of the coil spring 2 urges the pipes 3, 4 away from each other. In other words, the actuator is urged by the elastic force of the coil spring 2 in a direction for expansion along the axial direction. Since the actuator is urged along the axial direction thereof, the actuator is prevented from expanding in directions perpendicular to the axial direction when the actuator operates to be expanded along the axial direction. Accordingly, the displacement (operational amount) of the actuator in the axial direction is maximized as much as possible.

Figure 1B:
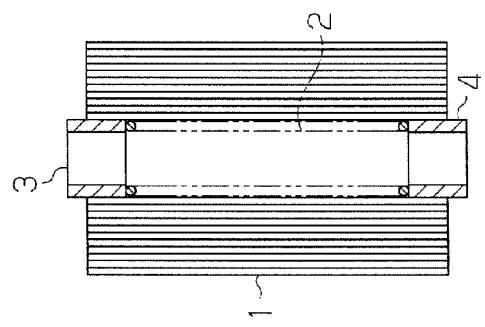
Figure 1C:
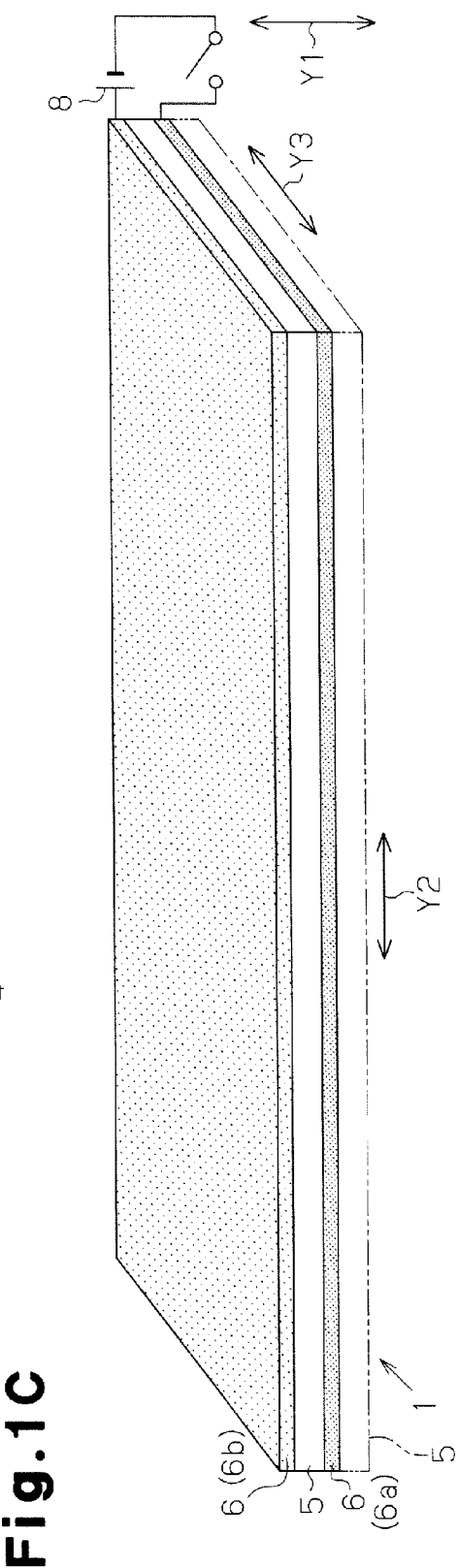

FIG. 1C conceptually shows a state in which the cylindrical sheet 1 is developed. The sheet 1 is formed by alternately stacking a plurality of dielectric rubber layers (dielectric elastomer layers) 5 and a plurality of conductive rubber layers 6 (6a, 6b) along the direction of thickness (direction of arrow Y1). The conductive rubber layers 6 are made of general-purpose rubber, and the dielectric elastomer layers 5 are made of a high polymer (such as a high polymer gel), such as polyrotaxane, in which more specifically, cross-linking points are movable. Of the conductive rubber layers 6a, 6b sandwiching each dielectric elastomer layer 5, the conductive rubber layer 6a is connected to a negative terminal of a power source 8, and the conductive rubber layer 6b is connected to a positive terminal of the power source 8. When voltage is applied to the conductive rubber layers 6a, 6b, the dielectric elastomer layers 5 are contracted in the thickness direction (direction of arrow Y1), while expanding in a direction perpendicular to the thickness direction (direction of arrow Y2 and direction of arrow Y3). When the application of voltage to the conductive rubber layer 6a, 6b is stopped, the dielectric elastomer layers 5 are restored, by the elasticity thereof, from the contraction along the thickness direction and the expansion along the directions perpendicular to the thickness direction.

The rolled cylindrical sheet 1 shown in FIGS. 1A and 1B is contracted and expanded along the axial direction of the cylindrical sheet 1 by executing or stopping application of voltage to the conductive rubber layers 6a, 6b (FIG. 1C), so that the sheet 1 is contracted and expanded. That is, when voltage is applied to the conductive rubber layers 6a, 6b, the cylindrical sheet 1 extends along the axial direction as shown in FIG. 1B. When voltage application to the conductive rubber layers 6a, 6b is stopped, the cylindrical sheet 1 is contracted along the axial direction from the expanded state shown in FIG. 1B to a contracted state shown in FIG. 1A. Such expansion and contraction of the cylindrical sheet 1 operates the actuator, so that the actuator is displaced along the axial direction.

The structure of the sheet 1 will now be described with reference to FIG. 2.

Figure 2:
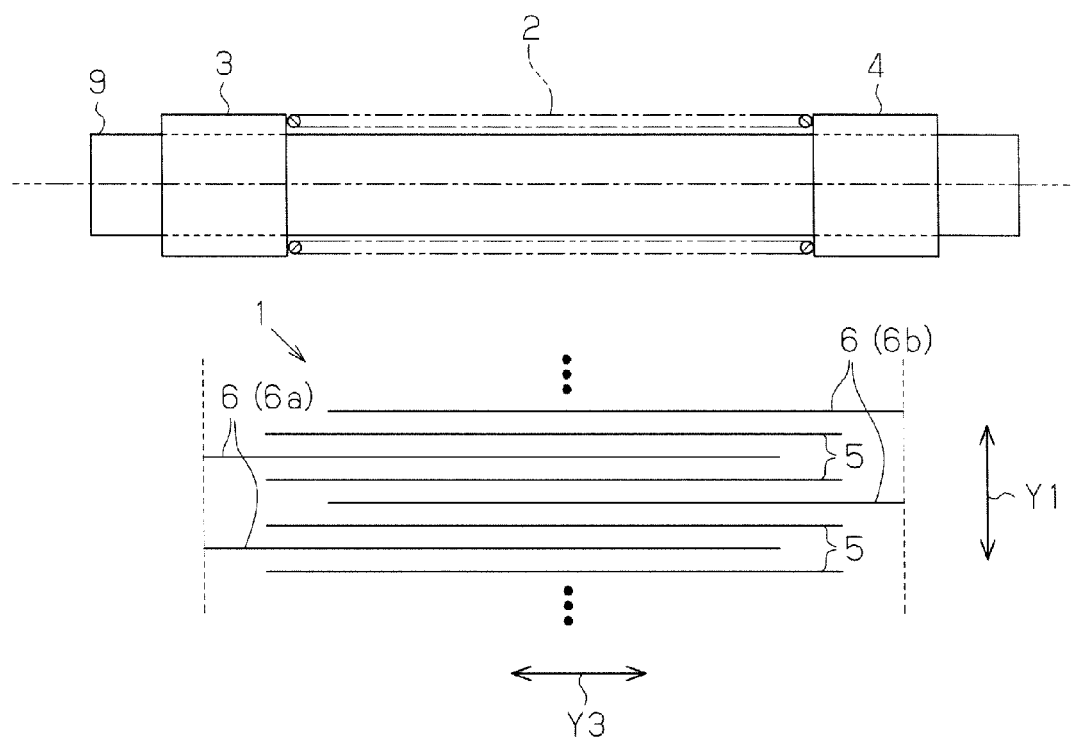
FIG. 2 is a schematic diagram of a developed state of the sheet, showing overlapping of the dielectric elastomer layers and the conductive rubber layers.

FIG. 2 is a schematic view of the sheet 1 in a developed state as viewed in the direction of arrow Y2 in FIG. 1C, showing overlapping of the dielectric elastomer layers 5 and the conductive rubber layers 6 (6a, 6b).

As shown in FIG. 2, the dielectric elastomer layers 5 are located substantially at the same position with respect to the direction of arrow Y3 in the sheet 1. In contrast, the conductive rubber layers 6 (6a, 6b) are located at displaced positions with respect to the direction of arrow Y3 (the left-right direction as viewed in FIG. 2). Specifically, of the conductive rubber layers 6 (6a, 6b), each of the conductive rubber layers 6a for being connected to a negative terminal is displaced leftward as viewed in FIG. 2 with respect to the direction of arrow Y3 relative to the dielectric elastomer layers 5, and each of the conductive rubber layers 6b for being connected to a positive terminal is displaced in the opposite direction to the rubber layers 6a relative to the dielectric elastomer layers 5, that is, displaced rightward as viewed in FIG. 2 with respect to the direction of arrow Y3.

The dielectric elastomer layers 5 and the conductive rubber layers 6 (6a, 6b) are stacked along the thickness direction as described above, and closely contact each other. The conductive rubber layers 6a for being connected to a negative terminal are stacked onto each other at the left portion in FIG. 2 to be electrically connected to each other. Also, the conductive rubber layers 6b for being connected to a positive terminal are stacked onto each other at the right portion in FIG. 2 to be electrically connected to each other. Therefore, to apply voltage to the conductive rubber layers 6 (6a, 6b), an electrode for connecting the conductive rubber layers 6a to the negative terminal of the power source 8 (FIG. 1C) only needs to be attached to one section of the conductive rubber layers 6a, and an electrode for connecting the conductive rubber layers 6b to the positive terminal of the power source 8 only needs to be attached to one section of the conductive rubber layers 6b.

A method for manufacturing the actuator will now be described.

The actuator manufacturing method includes a first step, in which a plurality of dielectric elastomer layers 5 and a plurality of the conductive rubber layers 6 (6a, 6b) are alternately stacked along the direction of thickness to form a sheet 1, and a second step, in which the sheet 1 formed in the first step is wrapped about a core 9 to form a rolled sheet 1. The first step and the second step will now be described.

[First Step]

In the first step, a coater 11 as shown in FIGS. 3A to 3D operates to alternately laminate dielectric elastomer layers 5 and conductive rubber layers 6 onto a film 12. The coater 11 is a device for applying material for forming dielectric elastomer layers 5 and conductive rubber layers 6 onto the film 12, and is movable in the direction of arrow Y2 and the direction of arrow Y3 in the drawing. Using the coater 11, dielectric elastomer layers 5 and conductive rubber layers 6 are alternately laminated on the film 12 through the following processes (A) to (E).

Figure 3:
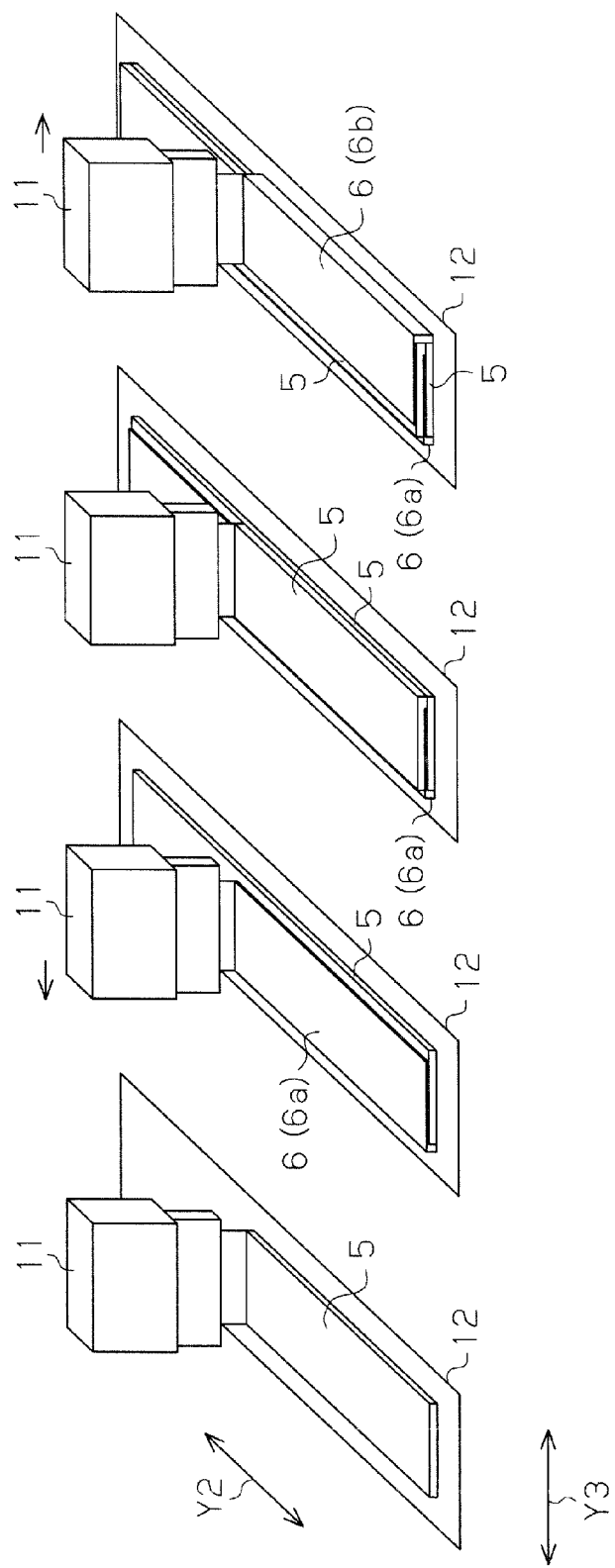
FIGS. 3A to 3D are schematic diagrams showing an operation of a coater in a first step.

Process (A): With the coater 11 fixed with respect to the direction of arrow Y3, the coater 11 applies material for forming dielectric elastomer layers 5 on the film 12 as shown in FIG. 3A, while moving along the direction of arrow Y2 relative to the film 12.

Process (B): The coater 11 is displaced leftward as viewed in the drawing from the position of the process (A). In this state, the coater 11 applies a material for forming a conductive rubber layer 6 onto the dielectric elastomer layer 5, which has been formed on the film 12 through the process (A), while being moved along the direction of arrow Y2.

Process (C): The coater 11 is operated at the same position and in the same manner as in the process (A), so that the material for forming a dielectric elastomer layer 5 is applied onto the conductive rubber layer 6, which has been formed on the dielectric elastomer layer 5 through the process (B), as shown in FIG. 3C.

Process (D): The coater 11 is displaced rightward as viewed in the drawing from the position of the process (C) (the same position as that in the process (A)). In this state, the coater 11 applies the material for forming a conductive rubber layer 6 onto the dielectric elastomer layer 5, which has been formed on the film 12 through the process (B), while being moved along the direction of arrow Y2, as shown in FIG. 3D.

Process (E): The processes (A) to (D) are repeated for a predetermined number of times.

Through the processes (A) to (E), the dielectric elastomer layers 5 and the conductive rubber layer 6 are alternately laminated on the film 12. Accordingly, one sheet 1 is formed in which dielectric elastomer layers 5 and conductive rubber layers 6 (6a, 6b) are alternately stacked along the direction of thickness as shown in FIG. 2.

[Second Step]

In the second step, to form a roll of the single sheet 1, the sheet 1 is wrapped about a core 9 as shown in FIG. 2.

Figure 4:
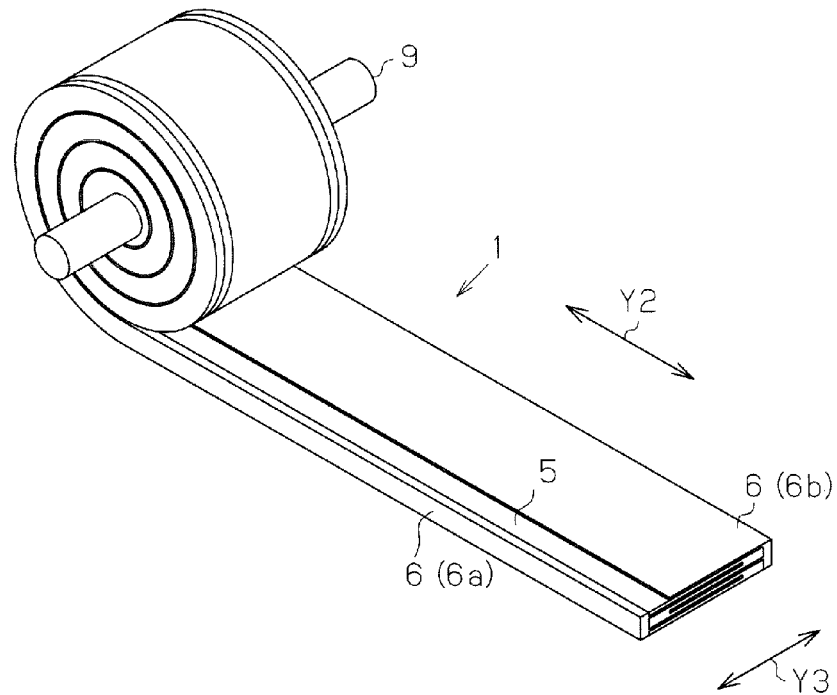
FIG. 4 is a schematic diagram of a second step, showing a state in which the sheet is being wrapped about the core.

Before wrapping the sheet 1, a coil spring 2 is attached to the outer circumferential surface of the core 9. Also, pipes 3, 4 are attached on both ends of the outer circumferential surface of the core 9 along the expansion and contraction direction of the coil spring 2 (left and right direction as viewed in FIG. 2). Accordingly, the core 9 is in a state of extending through the coil spring 2 and the pipes 3, 4, which are arranged on the outer circumferential surface. The core 9, to which the coil spring 2 and the pipes 3, 4 are attached, is arranged relative to the sheet 1 as shown in FIG. 2. The core 9 is rotated while the sheet 1 is wrapped about the core 9, so that the sheet 1 is rolled about the core 9 as shown in FIG. 4.

After the sheet 1 is rolled about the core 9 in the second step, the core 9 is removed from the rolled sheet 1. At this time, the coil spring 2 and the pipes 3, 4 remain inside the rolled sheet 1. The actuator is thus manufactured.

The thickness of each dielectric elastomer layer 5 for forming the sheet 1 in the first step is determined such that, when a voltage applicable for a house hold power source is applied to the conductive rubber layers 6 (6a, 6b), the actuator is expanded by the necessary amount (more accurately, such that the rolled sheet 1 is expanded by the necessary amount along the axial direction of the rolled sheet 1). The value of a voltage applicable for a household power source is, for example, up to 100 V or up to 200 V. Further, an example of the thickness of each dielectric elastomer layer 5 is 10 µm.

The total number of layers of the dielectric elastomer layers 5 and the conductive rubber layers 6 in the sheet 1 formed in the first step is determined so as to obtain the minimum thickness (for example, 50 to 100 µm) of the sheet 1 that allows the sheet 1 to be wrapped about the core 9 in the second step without tearing the layers 5, 6.

The above described embodiment has the following advantages.

(1) In the second step, when wrapping the single sheet 1 formed in the first step about the core 9 to form a roll, the single sheet 1 is formed by multiple dielectric elastomer layers 5 and multiple conductive rubber layers 6 (6a, 6b). Therefore, even if each of the dielectric elastomer layers 5 of the sheet 1 is made thin so as to reduce the voltage applied to the conductive rubber layers 6 (6a, 6b) so that the actuator operate adequately, the thickness of the single sheet 1 is prevented from being excessively reduced, for example, to less than 50 µm, as a whole. When wrapping the single sheet 1 around the core 9 in the second step, the wrapping can be uneven along the longitudinal direction of the core 9. In such a case, the load accompanying the uneven wrapping acts on the sheet 1. However, the load is dispersed to the multiple dielectric elastomer layers 5 in the sheet 1. This prevents the load from concentrating on one of the multiple dielectric elastomer layers 5 in the sheet 1. Accordingly, the dielectric elastomer layers 5 are prevented from being torn by concentration of the load.

(2) The conductive rubber layers 6a in the sheet 1 of the actuator are electrically connected to each other in the first step, so as to be connected to the negative terminal of the power source 8, and the conductive rubber layers 6b in the sheet 1 are electrically connected to each other in the first step, so as to be connected to the positive electrode of the power source 8. Therefore, of the electrodes for connecting the power source, the electrode for the negative terminal only needs to be attached to one of the conductive rubber layers 6a, and the electrode for the positive terminal only needs to be attached to one of the conductive rubber layers 6b. Therefore, compared to a case where conductive rubber layers 6 are separate from one another and electrodes are attached to each of the conductive rubber layers 6, the process for attaching electrodes is simplified.

(3) The thickness of each dielectric elastomer layer 5 for forming the sheet 1 in the first step is determined such that, when a voltage applicable for a house hold power source is applied to the conductive rubber layers 6 (6a, 6b), the actuator is expanded by the necessary amount (more accurately, such that the rolled sheet 1 is expanded by the necessary amount along the axial direction of the rolled sheet 1). Therefore, the manufactured actuator can be operated adequately by applying voltage from a house hold power source to the conductive rubber layers 6 (6a, 6b).

(4) The total number of layers of the dielectric elastomer layers 5 and the conductive rubber layers 6 in the sheet 1 formed in the first step is determined so as to obtain the minimum thickness of the sheet 1 that allows the sheet 1 to be wrapped about the core 9 in the second step without tearing the layers 5, 6. Accordingly, in the second step, the sheet 1, which has been formed in the first step, is wrapped about the core 9 without tearing any of the dielectric elastomer layers 5 and the conductive rubber layers 6 forming the sheet 1. Since the total number of layers in the sheet 1 formed in the first step is the minimum number required for preventing tearing of layers, the formation of the sheet 1 in the first step can be simplified as possible.

The above described embodiment may be modified as follows.

Figure 5A:
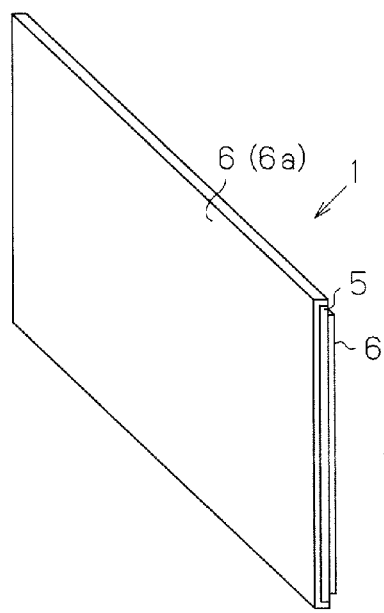
FIGS. 5A to 5D are schematic diagrams showing a modification of the first step.
Figures 5B, 5C, 5D:
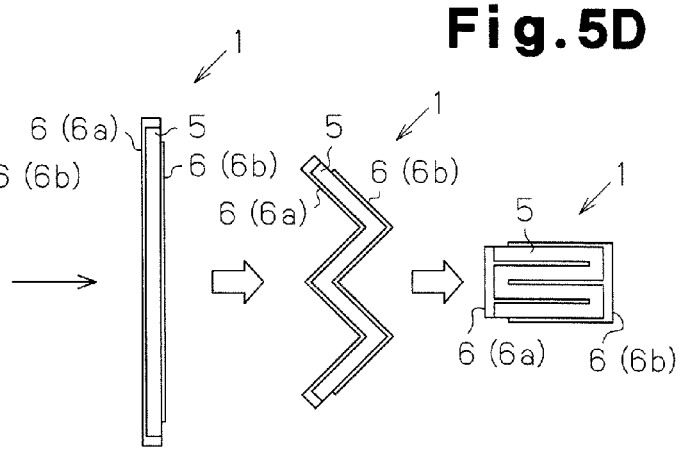

The first step may be replaced by the one that is conceptually described in FIGS. 5A to 5D. In this case, a conductive rubber layer 6a for being connected to the negative terminal of a power source 8 is formed on the front face of a dielectric elastomer layer 5 in a first step as shown in FIGS. 5A and 5B. Also, a conductive rubber layer 6b for being connected to the positive terminal of the power source is formed on the back face of the dielectric elastomer layer 5. In this state, the dielectric elastomer layer 5 and the conductive rubber layers 6a, 6b are folded in a bellows-like manner as shown in FIG. 5C, so that a sheet 1 shown in FIG. 5D is obtained, in which a plurality of dielectric elastomer layers 5 and a plurality of conductive rubber layers 6 (6a, 6b) are alternately stacked in the direction of thickness. Even if this modified first step is employed, each dielectric elastomer layer 5 is sandwiched between a conductive rubber layer 6a for being connected to the negative terminal of the power source 8 and a conductive rubber layer 6b for being connected to the positive terminal of the power source 8, so that a great number of layers are stacked. Among the stacked multiple layers, the conductive rubber layers 6a for being connected to the negative terminal of the power source 8 are electrically connected each other, and the conductive rubber layers 6b for being connected to the positive terminal of the power source 8 are electrically connected to each other. The same advantage as the advantage (2) of the above embodiment is therefore achieved.

The number of layers such as dielectric elastomer layers and conductive rubber layers 6 of the sheet 1 formed in the first step may be changed as necessary.

The thickness of one dielectric elastomer layer 5 when forming the sheet 1 in the first step may be changed as necessary.

The power source 8 is not limited to a house hold power source, for example, of 100 V or 200v, but may be another type of power source such as an industrial power source that is outside the standard for a household power source.

The conductive rubber layers 6a for being connected to the negative terminal of the power source 8 may be electrically separated from each other. In this case, an electrode for being connected to the negative terminal of the power source 8 is attached to each of the separate conductive rubber layers 6a.

The conductive rubber layers 6b for being connected to the positive terminal of the power source 8 may be electrically separated from each other. In this case, an electrode for being connected to the positive terminal of the power source 8 is attached to each of the separate conductive rubber layers 6b.

Therefore, the present examples and embodiments are to be considered as illustrative and not restrictive and the invention is not to be limited to the details given herein, but may be modified within the scope and equivalence of the appended claims.

The invention claimed is:

1. A method for manufacturing an actuator formed by rolling a single sheet in which dielectric elastomer layers and conductive rubber layers are stacked along a direction of thickness, wherein, when a voltage is applied to the conductive rubber layers, the actuator expands the rolled sheet along an axial direction of the rolled sheet, and when the application of the voltage is stopped, the actuator contracts the rolled sheet along the axial direction, the method comprising;

alternately stacking a plurality of dielectric elastomer layers and a plurality of conductive rubber layers along a direction of thickness, thereby forming the single sheet; and wrapping the single sheet formed in the step of alternately stacking about a core, thereby obtaining the rolled sheet, wherein some of the conductive rubber layers are connected to a positive terminal of a power source, and the other conductive rubber layers are connected to a negative terminal of the power source, and the step of alternately stacking includes:

supplying the conductive rubber layers for being connected to the positive terminal of the power source that are stacked onto each other while being displaced in the same direction relative to the dielectric elastomer layers; and supplying the conductive rubber layers for being connected to the negative terminal of the power source that are stacked onto each other while being displaced in the opposite direction to the direction in which the conductive rubber layers for being connected to the positive terminal of the power source are displaced relative to the dielectric elastomer layers.

2. The method for manufacturing an actuator according to claim 1, wherein a thickness of each dielectric elastomer layer for forming the single sheet in the step of alternately stacking is determined such that, when the voltage is applied to the conductive rubber layers by the power source, the rolled sheet is expanded by a necessary amount.

3. The method for manufacturing an actuator according to claim 1, wherein the number of stacked layers in the step of alternately stacking is determined so as to obtain a minimum thickness of the single sheet that allows the single sheet to be wrapped about the core in the step of wrapping the single sheet without tearing the plurality of dielectric elastomer layers and the plurality of conductive rubber layers.

4. A method for manufacturing an actuator formed by rolling a single sheet in which dielectric elastomer layers and conductive rubber layers are stacked along a direction of thickness, wherein, when a voltage is applied to the conductive rubber layers, the actuator expands the rolled sheet along an axial direction of the rolled sheet, and when the application of the voltage is stopped, the actuator contracts the rolled sheet along the axial direction, the method comprising;

alternately stacking a plurality of dielectric elastomer layers and a plurality of conductive rubber layers along a direction of thickness, thereby forming the single sheet; and wrapping the single sheet formed in the step of alternately stacking about a core, thereby obtaining the rolled sheet, wherein the step of alternately stacking includes supplying one of the conductive rubber layers for being connected to a positive terminal of a power source that is formed on a front face of one of the dielectric elastomer layers, and one of the conductive rubber layers for being connected to a negative terminal of the power source that is formed on a back face of the dielectric elastomer layer, and in this state, the dielectric elastomer layers and the conductive rubber layers are formed in a bellows-like manner, so that the plurality of the dielectric elastomer layers and the plurality of the conductive rubber layers are stacked onto each other in the direction of thickness to form the single sheet.

5. The method for manufacturing an actuator according to claim 4, wherein a thickness of each dielectric elastomer layer for forming the single sheet in the step of alternately stacking is determined such that, when the voltage is applied to the conductive rubber layers by the power source, the rolled sheet is expanded by a necessary amount.

6. The method for manufacturing an actuator according to claim 4, wherein the number of stacked layers in the step of alternately stacking is determined so as to obtain a minimum thickness of the single sheet that allows the single sheet to be wrapped about the core in the step of wrapping the single sheet without tearing the plurality of dielectric elastomer layers and the plurality of conductive rubber layers.

7. A method for manufacturing an actuator formed by rolling a single sheet in which dielectric elastomer layers and conductive rubber layers are stacked along a direction of thickness, wherein, when a voltage is applied to the conductive rubber layers, the actuator expands the rolled sheet along an axial direction of the rolled sheet, and when the application of the voltage is stopped, the actuator contracts the rolled sheet along the axial direction, the method comprising;

alternately stacking a plurality of dielectric elastomer layers and a plurality of conductive rubber layers along a direction of thickness, thereby forming the single sheet; and wrapping the single sheet formed in the step of alternately stacking about a core, thereby obtaining the rolled sheet, wherein the step of wrapping the single sheet includes:

prior to wrapping of the single sheet about the core, providing a coil spring on an outer circumferential surface of the core, and providing a pair of pipes on the outer circumferential surface of the core, each pipe being at one of both ends along the direction of expansion and contraction of the spring; and removing the core from the rolled sheet after wrapping the single sheet about the core, which has, on the outer circumferential surface thereof, the coil spring and the pipes.

8. The method for manufacturing an actuator according to claim 7, wherein a thickness of each dielectric elastomer layer for forming the single sheet in the step of alternately stacking is determined such that, when the voltage is applied to the conductive rubber layers by a power source, the rolled sheet is expanded by a necessary amount.

9. The method for manufacturing an actuator according to claim 7, wherein the number of stacked layers in the step of alternately stacking is determined so as to obtain a minimum thickness of the single sheet that allows the single sheet to be wrapped about the core in the step of wrapping the single sheet without tearing the plurality of dielectric elastomer layers and the plurality of conductive rubber layers.

* * * * *